United States Patent [19]

Bonis

[11] Patent Number: 5,144,592
[45] Date of Patent: Sep. 1, 1992

[54] ULTRASONIC TRANSMISSION-RECEPTION SYSTEM

[75] Inventor: Marc Bonis, Montlhéry, France

[73] Assignee: Commissariat A L'Energie Atomique, Paris, France

[21] Appl. No.: 721,088

[22] Filed: Jun. 25, 1991

[30] Foreign Application Priority Data

Jun. 27, 1990 [FR] France .................. 90 08110

[51] Int. Cl.[5] .............................................. G01S 15/00
[52] U.S. Cl. ...................................... 367/87; 367/903; 367/137
[58] Field of Search ............ 367/13, 100, 87, 903, 367/137; 73/1 DV

[56] References Cited

U.S. PATENT DOCUMENTS 4,566,331  1/1986  Schroeder ............................ 73/632
4,623,838  11/1986 Nakamura ........................... 364/483
4,696,425  9/1987  Landes ................................ 310/317

Primary Examiner—Daniel T. Pihulic
Attorney, Agent, or Firm—Michael N. Meller

[57] ABSTRACT

An ultrasonic transmission-reception system having a piezoelectric transducer for at least transmitting ultrasonic waves, a current generator for exciting the transducer so that it transmits an ultrasonic wave and electronic processing means able to determine in an approximate manner and store at least one current generator exciting signal. The exciting signal being associated with a reference object and leads to a predetermined detected ultrasonic wave shape from said object following the interaction of said object with the ultrasonic wave produced by the transducer as a result of the excitation of the current generator.

12 Claims, 10 Drawing Sheets

ULTRASONIC TRANSMISSION-RECEPTION SYSTEM

DESCRIPTION

The present invention relates to an ultrasonic transmission-reception system. It is more particularly used in the field of ultrasonic testing and inspection (testing or welds, mechanical parts, etc.).

Various ultrasonic transmission-reception systems are known. Each of the known systems has a piezoelectric transducer for at least the transmission of ultrasonic waves, as well as an electric current generator for exciting the transducer so that it transmits an ultrasonic wave.

For so-called broad band piezoelectric ultrasonic transmission, the exciting current generator still uses the principle of the rapid charging (or discharging) of the shunt capacitor of the transducer, followed by the slower speed, exponential discharging (or charging) of said capacitor. The latter is generally regulatable and is known as damping.

The rapid switching necessary for such an ultrasonic transmission used to be carried out by means of a thyristor. At present, use is made of a MOS power transistor or a plurality of transistors.

A system is also known, which comprises an exciting current generator known as a unipolar transmitter, which has the special feature of not instantaneously recharging the shunt capacitor of the piezoelectric transducer after having violently discharged the same. In said unipolar transmitter, the recharging of the capacitor takes place slowly following the reception of the expected ultrasonic echo.

The known ultrasonic transmission-reception systems suffer from several disadvantages.

Firstly, these systems offer no possibility of acting on the shape of the ultrasonic wave transmitted by the piezoelectric transducer, except the regulation of the rear exponential front of the electric exciting pulse of said transducer (damping), whose action on the transmitted wave shape is relatively limited.

In addition, the damping of the transducer, which is indispensable when it is wished to operate in a broad band, is largely carried out by the physical damping of the material to the rear of the piezoelectric pellet of the transducer. This damping is always imperfect, particularly in the case of transducers designed for operating at low frequencies.

Various electrical solutions utilizing transformers and inductors are used for electrically compensating the imperfection of this physical damping and for simultaneously adapting the transducer to a transmission line, whose characteristic impedance is generally 50 ohms.

In certain cases such as objective can virtually be achieved, but in all cases the passive filter developed is only appropriate for a given transducer and for a given ultrasonic wave shape.

Finally, as it is theoretically possible by using a purely passive filter to bring the impedance of a piezoelectric pellet to a real value of 50 ohms over a wide frequency band, the adapting of the transducer is always imperfect and consequently there is a deterioration to the efficiency of the ultrasonic transmitters.

The present invention aims at obviating the above disadvantages.

It relates to an ultrasonic transmission-reception system comprising ultrasonic transmission-reception means having a piezoelectric transducer for at least transmitting ultrasonic waves and an electric current generator for exciting the transducer so that it transmits an ultrasonic wave, characterized in that it also has electronic processing means able to determine in an approximate manner and store at least one current generator exciting signal, the latter being associated with a reference object and leading to a predetermined shape of the detected ultrasonic wave from the said object following the interaction of the latter with the ultrasonic wave produced by the transducer as a result of the excitation of the current generator.

Thus, the system according to the invention uses a completely different principle from those used in the known systems referred to hereinbefore. Instead of exciting the ultrasonic transducer by a signal which is virtually always the same, the system according to the invention operates in two stages.

In a first stage, it determines the exciting signal of its current generator as a function of a criterion specified by the user. In a second stage, the system produces the electric current corresponding to said exciting signal (which has been stored) in order to excite the piezoelectric transducer and carry out ultrasonic testing.

The criterion to be specified by the user relates to the ultrasonic wave shape from the reference object following the interaction thereof with the ultrasonic wave produced by the excited transducer.

When working in reflection, the reference object is a reference reflector and the criterion to be specified by the user is the shape of the ultrasonic echo supplied by said reference reflector.

The reference object can e.g. be an "infinite" plane, an "infinite" half-plane (edge of a crack), a disk, a ball, a cone, a flat-bottomed hole, an artificial defect or a real defect in a mechanical part.

The shape of the ultrasonic wave from the reference object can be defined in time form (as a function of time) or in spectral form (as a function of the ultrasonic frequency), as a function of whether the user wishes to impose constraints on the time content or on the spectral content of the ultrasonic wave from the reference object.

The Expert is well aware of the passage from the time form to the spectral form of a wave and vice versa (direct and reverse Fourier transformation).

The system according to the invention is an "intelligent" system in the sense that it adapts both to physical imperfections of the piezoelectric transducer used and to the ultrasonic testing conditions and that it determines the excitation of the piezoelectric transducer with a view to receiving an ultrasonic wave with a shape fixed by the user for a chosen reference object.

The present invention makes it possible to form a data bank (current generator exciting signals) making it possible, during the testing by ultrasonics of a part, whose faults or defects are generally of a known type, to recognize said faults.

According to a preferred embodiment of the system according to the invention, electronic processing means are provided for determining the inverse function $H^{-1}$ of the transfer function H of the process which, at an exciting signal X of the current generator, associates the signal $Y=H(X)$ detected by the reception means, said function $H^{-1}$ being determined on the basis of an initial exciting signal Xo of the current generator and the detected signal $H(Xo)$, assuming the function H to be linear and independent of time and then by an iteration method, an approximation Xn of said exciting signal associated with the reference object, on the basis of a signal X1 taken as equal to the image, by the function $H^{-1}$, of the given ultrasonic wave shape and by correcting, during each iteration stage, the approximation of the exciting signal of the current generator obtained in the preceding stage by the image, by the function $H^{-1}$ of the error committed in said preceding stage on the given ultrasonic wave shape.

Preferably, the current generator has at least one bidirectional electric current source for exciting the transducer. Each bidirectional source can be constituted by two unidirectional current sources. Each unidirectional source can incorporate a MOS transistor. The piezoelectric transducer can be used for the transmission and reception of ultrasonic waves.

According to an embodiment of the system according to the invention, the current generator excites the transducer asymmetrically.

According to another embodiment, the current generator incorporates two bidirectional current sources for exciting the transducer symmetrically.

In the case where the transducer is intended for the transmission and reception of ultrasonic waves, the transmission-reception means can also incorporate means for amplifying signals detected by said transmission-reception means and switching means able to isolate the amplifying means from the transducer when the latter transmits an ultrasonic wave.

In the case in question, the transmission-reception means can also incorporate means for controlling the current generator, said control means receiving at the input signals from electronic processing means and are used for exciting the current generator and supplying at the output signals for exciting the current generator and other switching means able to isolate the control means from the transducer, when the latter receives an ultrasonic wave.

Preferably, in order to reduce the number of iterations necessary for the determination of the exciting signal associated with the reference object and which corresponds to the given ultrasonic wave shape, electronic processing means are also provided for determining a transformation of the exciting signal of the current generator, whose composition is approximately linear with the transfer function H.

In this case, the system according to the invention can also incorporate an electrical resistor and a two-position switch, namely a first position in which said switch connects the current generator to the electrical resistor to feed into the latter the current supplied by the current generator and a second position in which said switch connects the current generator to the transducer for exciting the latter, the electronic processing means then being able to determine, when the switch is in the first position, and to store a transformation of the exciting signal of the current generator, which enables the current supplied by said current generator to vary linearly as a function of the current generator exciting signal.

BRIEF DESCRIPTION OF THE DRAWINGS

The invention is described in greater detail hereinafter relative to non-limitative embodiments and the attached drawings, wherein show.

Figure 1:
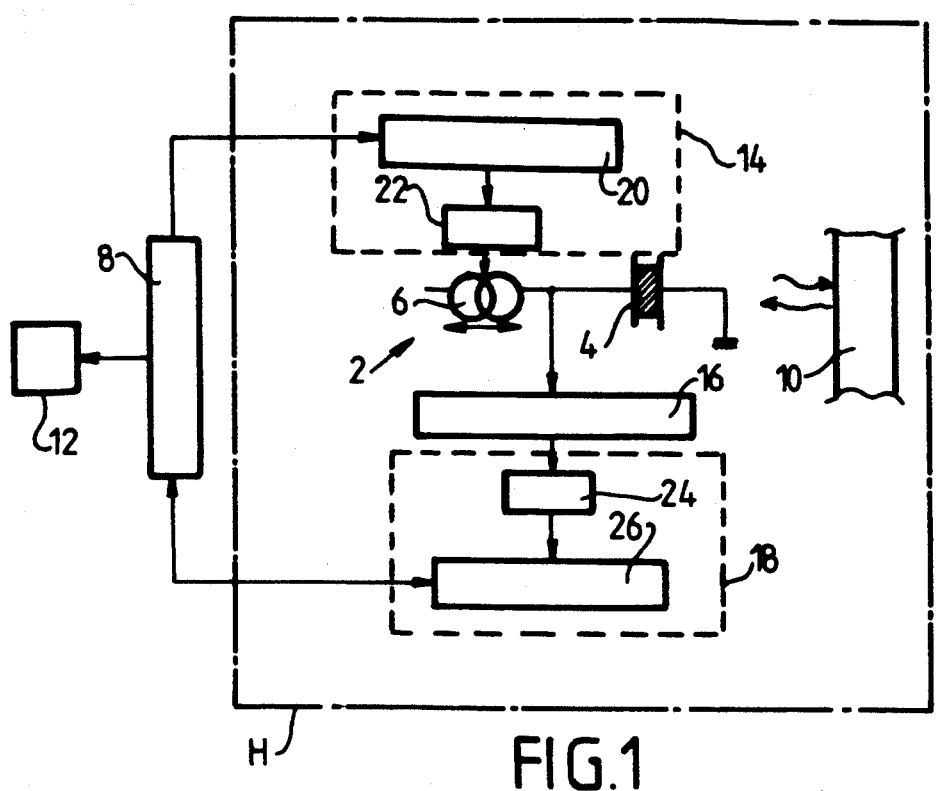
FIGS. 1 to 3 Diagrammatically the systems according to the invention.

The system according to the invention diagrammatically shown in FIG. 1 has ultrasonic transmission-reception means 2 comprising a piezoelectric transducer 4 for the transmission and reception of ultrasonic waves and an electric current generator 6 for exciting the transducer in order that it transmits an ultrasonic wave.

The system shown in FIG. 1 also has electronic processing means 8 able to determine in an approximate manner and store a digital exciting signal for the current generator 6 (which then in turn excites the piezoelectric transducer).

This digital exciting signal is associated with a reference reflector 10 and calculated by the electronic processing means 8 in order to lead to a predetermined detected ultrasonic echo shape, said echo being transmitted by the reference reflector when the latter receives an ultrasonic wave from the excited piezoelectric transducer.

Obviously, these calculations can be carried out for a plurality of reference reflectors, which leads to a plurality of digital exciting signals for the current generator 6, each exciting signal being associated with a reference reflector.

This leads to the formation of a data bank in the electronic processing means 8. This data bank is usable for subsequently recognizing faults and defects in ultrasonically tested parts tested by using the system according to FIG. 1 (provided that these faults correspond to exciting signals forming part of the data bank).

The results of the test or inspection are displayed on display means 12 used for equipping the electronic processing means 8.

The transmission-reception means 2 also comprise means 14 for controlling the current generator 6, means 16 for amplifying the electrical signals supplied by the transducer 4 when the latter detects an ultrasonic echo and means 18 for digitizing amplified signals.

The control means 14 receive at the input digital signals from electronic processing means 8 and transform these digital signal into analog signals for controlling the current generator. The control means 14 comprise a logic and microprocessing interface 20 followed by digital-analog conversion means.

The interface 20 receives at the input the digital signals from the electronic processing means 8 and the conversion means 22 supply analog control signals of the current generator 6. The digitizing means 18 comprise analog-digital conversion means 24 followed by a logic and microprocessing interface 26. The conversion means 24 receive at the input an analog signal from the amplification means 16 and the interface 26 supplies to the electronic processing means 8 a digital signal corresponding to said analog signal.

It is precisely such a digital signal which is associated with the reference reflector 10 by users of the system shown in FIG. 1 and as a function of which the electronic processing means 8 determine a digital exciting signal of the current generator 6 leading on the return path to the digital signal associated with said reference reflector and subsequently referred to as the reference signal.

A piezoelectric transducer usable for broad band, high power ultrasonic transmission, used in the testing of significant steel thicknesses, has a shunt capacitor with a value exceeding abut 10 nanofarads. Consequently, when the transducer 4 is a transducer intended for broad band ultrasonic transmission, for exciting the transducer 4 in analog manner, preference is given to the use of a current generator constituted by a current source, which is bidirectional, linear, has a broad band and a maximum intensity.

Figure 2:
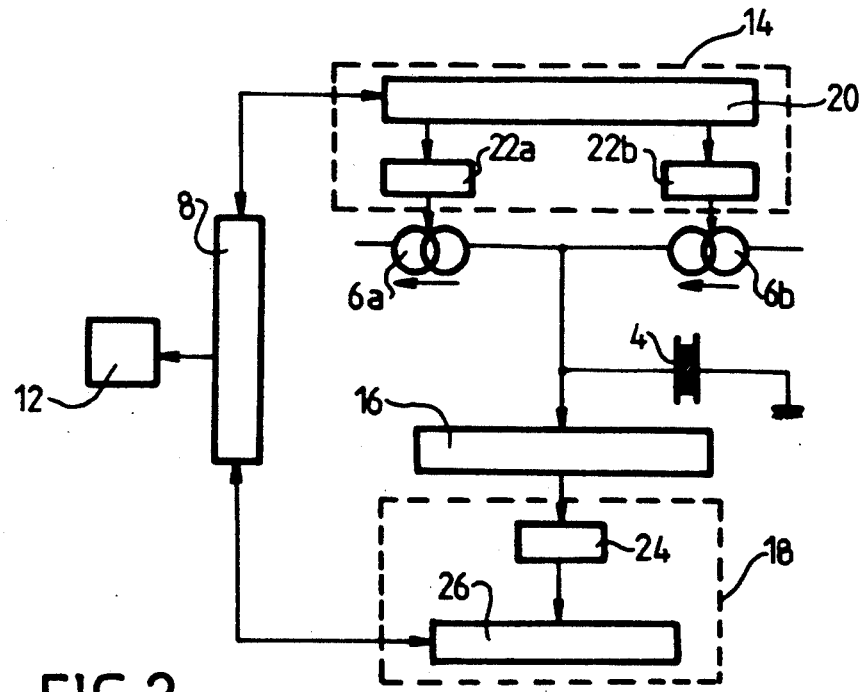

For producing such a bidirectional source 6, it is possible to use two unidirectional current sources 6a, 6b, as can be seen in FIG. 2. In this case, the digital-analog conversion means 22 are constituted by two analog-digital converters 22a, 22b, which are respectively associated with the unidirectional sources 6a, 6b, as can also be seen in FIG. 2.

Figure 3:
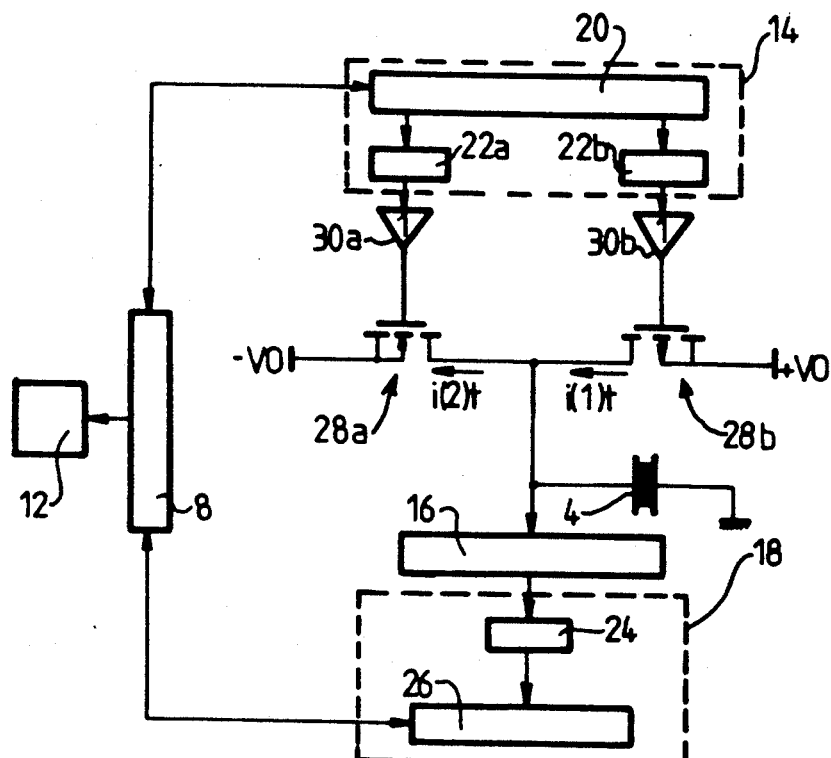

Finally, for obtaining high intensity, electric currents, the unidirectional current sources 6a, 6b are preferably respectively constituted by MOS power transistors 28a and 28b, as can be seen in FIG. 3.

For example made of an asymmetrical excitation of the piezoelectric transducer 4, as can be seen in FIGS. 1 to 3.

In FIG. 3 it is possible to see that the transistor 28a is a N channel MOS transistor, whose source is raised to a negative potential −VO and the transistor 28b is a P channel MOS transistor, whose source is raised to a positive potential +VO.

The drains of the transistors 28a and 28b are connected to one another, as well as to a terminal of the piezoelectric transducer 4, whose other terminal is earthed or grounded.

The gate of the transistor 28a is connected to the output of the digital-analog converter 22a across a power adapting stage 30a. In the same way, the gate of the transistor 28b is connected to the output of the digital-analog converter 22b across a power adapting stage 30b.

It can also be seen that the terminal of the transducer 4, which is connected to the drain of the two transistors 28a and 28b is also connected to the input of the amplification means 16.

An explanation will now be given with the aid of FIG. 4 of the convergent algorithm used in the electronic processing means 8 for determining the digital exciting signal leading to the digital reference signal imposed by users of the system. This digital reference signal is designated $Yr(t)$, t representing time.

Figure 4:
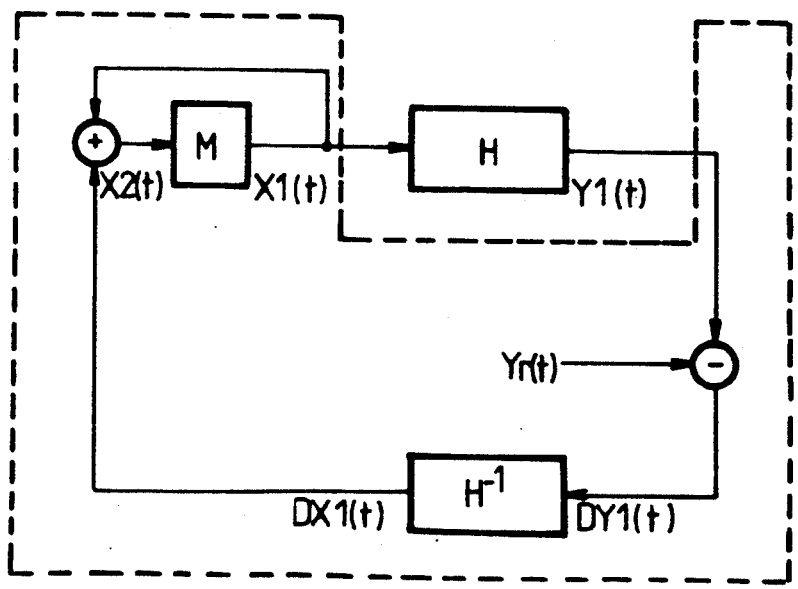
FIG. 4 Diagrammatically a calculating algorithm used in the systems shown in FIGS. 1 to 3.

All that is surrounded by dots in FIG. 4 corresponds to calculations performed in the electronic processing means or computer 8.

In FIG. 4, the block M represents a buffer storage stage (part of the computer memory) in which is stored the result obtained after each iteration of the algorithm. The block H represents the entire non-linear physical process which takes place between the obtaining of the result $Xk(t)$ from stage k of the sequence of iterations and which leads to the digital exciting signal of the current generator 6, and the obtaining of the digital signal $Yk(t)$ supplied to the computer 8 by the output of the digitizing means 18 after detecting the ultrasonic echo induced by the signal $Xk(t)$, k being an integer at least equal to 1.

This physical process corresponds to that part of FIG. 1 which is defined by a broken line.

In FIG. 4, the block $H^{-1}$ represents the inverse, reverse or reciprocal function, designated $H^{-1}$, of the transfer function, designated H and corresponding to said physical process.

When using the algorithm in the computer 8, the buffer stage M is initially loaded by an appropriately chosen digital signal $Xo(t)$ (in a manner to be explained hereinafter) for covering the entire target-spectral band.

An initial shot is then carried out with $Xo(t)$, which produces an initial ultrasonic echo which, after detection, amplification and digitization, supplies a signal $Yo(t)$, which is therefore equal to $H(Xo(t))$. Knowing $Xo(t)$ and $Yo(t)$, the computer 8 determines and stores the function $H^{-1}$ assuming that the function H is a linear operator and which is invariant in time, i.e. independent of time.

Then (stage 1 of the sequence of iterations), the computer 8 determines and loads into the buffer stage M the signal $X1(t)$, so that:

$$X1(t) = H^{-1}(Yr(t)).$$

Bearing in mind the non-linearity of the physical transfer function H, $X1(t)$ is only an approximate value of the sought exciting signal.

A shot is then carried out with the signal $X1(t)$, which makes it possible to obtain a signal $Y1(t)$ equal to $H(X1(t))$.

On the basis of $Y1(t)$ and $Yr(t)$, the computer 8 determines an error signal $DY1(t)$, so that:

$$DY1(t) = Yr(t) - Y1(t).$$

On the basis of this error signal $DY1(t)$, which results from the non-linearity of the transfer function H, the computer 8 determines a correction $DX1(t)$ of the signal $X1(t)$, so that:

$$DX1(t) = H^{-1}(DY1(t)).$$

Then (stage 2 of the sequence of iterations), the computer 8 determines a new approximation $X2(t)$ of the sought exciting signal, so that:

$$X2(t) = X1(t) + DX1(t)$$

and loads the said signal $X2(t)$ into the buffer stage M.

A shot is then carried out with the signal X2(t) for leading to an approximation X3(t) of the sought exciting signal and so on.

The sequence of the general term Xk(t) converges and the iterations are stopped at a stage n at which the standard of the error signal DYn(t) is below a value specified by the users.

As the error signal DYn(t) is a group of numerical values, it is possible to take as the standard the largest of the absolute values of these numerical values. The value specified by users is e.g. equal to one thousandth of the peak amplitude.

The signal Xn(t) is stored in the computer 8 and taken as the current generator exciting signal for carrying out all or part of the ultrasonic testing of a part and, if the result of the test corresponds to Yr(t), from it is deduced that the reference reflector 10 is present in the checked or tested part.

The convergence of the sequence of general term Xk(t) increases in speed as the transfer function H is slightly non-linear.

An explanation will be given hereinafter of the choice of the signal Xo(t), which is initially loaded into the buffer stage M.

This signal Xo(t) is in fact a sequence of numerical values forming a sample formed whilst respecting the rules imposed by the Shannon theorem.

The signal Xo(t) is chosen in such a way that the extent of its spectral support SXo at least covers the extent of the spectral support Sr of the reference signal Yr(t), which is itself chosen equal to the spectral support SH of the transfer function H.

The term "spectral support of a signal x(t)", is understood to mean the frequency range f outside which the Fourier transform $\tilde{x}(f)$ of x(t) is quasi-zero, i.e. for example below one thousandth of the maximum amplitude.

It is pointed out that the spectral support SH of H is a physical data dependent on the transducer of the electronic equipment used and the reference reflector. Thus, e.g. a signal Xo(t) is chosen in such a way that:

$Xo(t) = +1$ if $0 \leq t \leq To$ with $To > 0$ $Xo(t) = -1$ if $-To \leq t < 0$ $Xo(t) = 0$ if $t < -To$ or $t > To$.

The transducer is excited with the aid of said signal Xo(t) and determination takes place of the spectral support SYo of the signal Yo(t) corresponding to Xo(t). If SYo if strictly included in SXo, then it is certain that SYo is equal to SH. If SYo is equal to SXo, excitation again takes place of the transducer with a signal Xo(t), whose spectral support is more extensive, which corresponds to a reduction of To in the aforementioned example and so on until a signal Yo(t) is obtained, such that SYo is strictly included in SXo.

SH is then known and it is equal to said spectral support SYo. It is then possible to choose the reference signal Yr(t).

To do this, the first stage consists of choosing a reference echo form or shape, i.e. a function Yr(t), whose time scale and amplitude are parameters to be fixed. Thus, e.g. a Hanning window is chosen as the reference echo shape.

The knowledge of SH makes it possible to fix the parameters in question, because the spectral support Sr of Yr(t) has been chosen equal to SH.

Preferably, acceleration takes place of the convergence of the sequence of general term Xk(t), i.e. the number of stages of the iteration sequence is reduced, particularly in the case where the bidirectional current source, which supplies a current i(t) for exciting the piezoelectric transducer 4, is constituted by two MOS power transducers respectively forming two unidirectional current sources (case of FIG. 3).

Indeed, it is known that a MOS power transistor is an electronic device, whose transconductance is a non-linear function.

In order to speed up the convergence, the computer 8 determines, prior to the calculations leading to Xn(t), a transformation of the signal X(t), produced by the computer 8 for the excitation of the transducer 4 and which is such that the application of the transfer function H to the thus transformed signal gives a signal Y(t), which is a slightly non-linear function of X(t).

To do this, the system is provided with an electrical resistor 32 (FIG. 5), which can be approximately 50 ohms, as well as a switch 34 having two positions designated (1) and (2).

This switch 34 feeds current i(t) either to a terminal of the resistor 32, whose other terminal is earthed or grounded (position (1) of the switch 34) or to a terminal of the piezoelectric transducer 4, whose other terminal is grounded (position (2) of switch 34).

It is pointed out that the current i(t) is the sum of a positive current i1(t), supplied by the source 6b, and a negative current i2(t) supplied by the source 6a.

The voltage appearing between the terminals of the piezoelectric transducer 4 when the latter receives an ultrasonic echo from the reference reflector is designated v(t). The latter is amplified by the amplification means 16 (voltage amplifier).

The passage of the switch 34 from position (1) to position (2) and vice versa can be controlled by the computer 8.

Experience has shown that the conversion of i(t) by the piezoelectric transducer 4 into an ultrasonic vibration, the propagation of the vibration, the reflection of the latter onto an object (e.g. fault), the reverse conversion of the echo received by the piezoelectric transducer 4 into a voltage v(t) and finally the amplification of said voltage v(t) by the amplification means 16 (voltage amplifier) are slightly non-linear operations.

Consequently, to speed up the convergence, the computer 8 determines, prior to the calculations leading to Xn(t), a transformation of the signal X(t), produced by the computer 8 for exciting the transducer 4 and which is such that the application of the transverse signal H to the thus transformed signal gives a current i(t), which is a slightly non-linear function of X(t).

In the case of FIGS. 2 and 3 (use of two unidirectional current sources), the transformation is a double transformation consisting of two correction functions F1 and F2 respectively associated with i1(t) and i2(t).

In order to determine the correction functions F1 and F2, the switch 34 is placed in position (1). In the position (1), the current i(t) supplied by the bidirectional current source is supplied to the pure electrical resistor 32 in such a way that the signal Y(t) is proportional to i(t).

In order to determine the correction functions F1 and F2, a chirp-type signal X(t) is used, so that:

if X(t) is positive, i(t) is positive, i(t) then being equal to i1(t) and if X(t) is negative, i(t) is negative, i(t) then being equal to i2(t).

In a first stage, the computer 8 supplies the particular signal X(t) to each of the two digital-analog converters 22a and 22b of the control means or generator 14 (across the interface 20) and receives the corresponding signal Y(t), which is proportional to i(t).

The computer 8 is then able to determine two non-linear functions G1 and G2, so that:

$$i(t) = i1(t) = G1(X(t)) \text{ for } X(t) > 0$$

$$i(t) = i2(t) = G2(X(t)) \text{ for } X(t) > 0.$$

The function G1 (respectively G2) corresponds to the non-linearity of the unidirectional source 6b (respectively 6a).

In a second stage, the computer 8 determines and stores the correction functions F1 and F2, so that:

$$G1(F1(X(t))) = K.X(t) \text{ for } X(t) \geq 0$$

$$G2(F2(X(t))) = K.X(t) \text{ for } X(t) < 0$$

K being a proportionality constant.

After the correction functions F1 and F2 have been determined and stored, the switch 34 is placed in position (2).

The current source 6a, 6b then supplies the piezoelectric transducer 4 and the latter is placed on front of the reference reflector 10 to determine the signal Xn(t).

At each stage k of the sequence of iterations, the signal Xk(t) is previously transformed by the functions F1 and F2 before the process H is applied thereto, which leads to a faster convergence than in the case of the absence of a prior transformation by the functions F1 and F2.

Hereinbefore, various signals considered such as X(t), Xk(t), Y(t) and Yk(t) have been designated in the form of continuous functions f(t) of time t, but in actual fact the calculations are carried out on "discreet time" signals, which are associated therewith, i.e. on sequences of numbers of type f(m.Te), in which Te represents a sampling period (function of the spectral extent of the processed signals). This association is obviously carried out respecting the rules imposed by the Shannon theorem.

Figure 6:
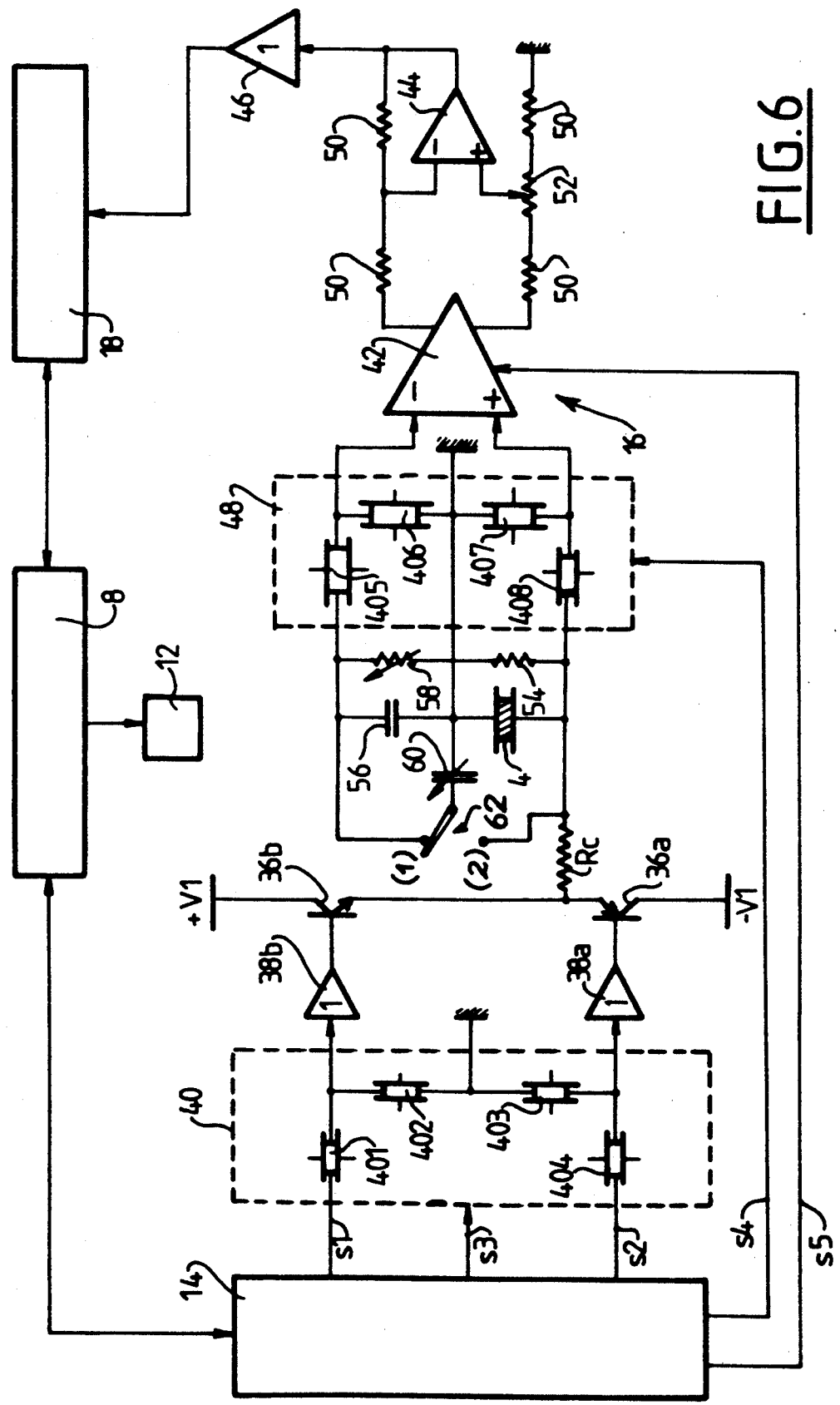
FIG. 6 A diagrammatic view of an embodiment of the system according to the invention using bipolar transistors for asymmetrically exciting the piezoelectric transducer of the system shown in FIG. 6.

FIG. 6 diagrammatically shows an embodiment of the system according to the invention, in which the piezoelectric transducer 4 is asymmetrically excited, one of its terminals being grounded. Moreover, the system diagrammatically shown in FIG. 6 has a bidirectional current source obtained by means of two bipolar power transistors 36a and 36b. These transistors 36a and 36b are controlled by the computer 8, across the generator 14, and the signals supplied by the transducer 4 are amplified by the amplification means 16 and then supplied to the computer via the digitizer 18.

The transistor 36a (respectively 36b) receives control signals from the generator 14 via a power adapting stage 38a (respectively 38b).

An analog isolating switch 40, whose function will be explained hereinafter, is interposed between the outputs of the generator 14 and the power adapting stages 38a and 38b.

The amplification means 16 comprise a preamplifier 42 followed by an amplifier 44, whose output supplies amplified signals to the digitizer 18 across a power adapting stage 46.

Another analog isolating switch 48, whose function will be explained hereinafter, is interposed between the transducer 4 and the preamplifier 42.

In the embodiment shown in FIG. 6, the transistor 36a is of the PNP type and the transistor 36b is of the NPN type. The emitters of these transistors are connected to one another, the collector of the transistor 36a being raised to a negative potential −V1, whilst the collector of the transistor 36b is raised to a positive potential +V1. The base of the transistor 36a is connected to the output of the adapting stage 38a, whilst the base of the transistor 36b is connected to the output of the adapting stage 38b.

In a non-limitative, informative manner, in the embodiment shown in FIG. 6:

the generator 14 is a double output, arbitrary function generator marketed by the LECROY company under reference 9100, the digitizer 18 is formed by a device marketed by the TEKTRONIX company under reference 7612, each of the switches 40 and 48 is of the type marketed by the HARRIS company under reference HI-201HS, each of the adapting stages 38a, 38b and 46 is of the type marketed by the HARRIS company under reference HA-5002, the preamplifier 42 is a differential output, programmable gain differential video preamplifier of the type marketed by RTC under reference NE 592 (gains 0, 100 and 400), and the amplifier 44 is a differential amplifier of the type marketed by the HARRIS company under reference HA-2539.

The use of the LECROY generator and the TEXTRONIX device referred to hereinbefore makes it possible to produce and digitize signals up to $100 \times 10^6$ samples per second, which covers most of the applications in the ultrasonic testing field.

In the embodiment shown in FIG. 6, the analog isolating switch 40 is constituted by four elementary switches 401, 402, 403, 404. In the same way, the analog isolating switch 48 is formed from four elementary switches 405, 406, 407 and 408.

One terminal of the switch 401 is connected to the first output s1 of the generator 14 and the other terminal of said switch 401 is connected to the input of the adapting stage 38b and to a terminal of the switch 402, whose other terminal is connected to a terminal of the switch 403 and is grounded. The other terminal of said switch 403 is connected to the input of the adapting stage 38a, as well as to a terminal of the switch 404, whose other terminal is connected to the second output s2 of the generator 14.

It can be seen in FIG. 6 that the generator 14 has auxiliary outputs s3, s4 and s5, which serve to respectively supply logic control signals for the switch 40, logic control signals for the switch 48 and gain control signals for the preamplifier 42. The preamplifier 42 and the amplifier 44 are associated with a network comprising four identical electrical resistors 50, as well as a potentiometer 52.

The inverting input of the amplifier 44 is connected to the output thereof across the first of the said resistors 50 and to one of the differential outputs of the preamplifier 42 across the second of said resistors 50.

The non-inverting input of the amplifier 44 is connected to the cursor of the potentiometer 52 and a terminal of the latter is grounded across the third of the resistors 50, whilst the other terminal of the potentiometer 52 is connected to the other differential output of the preamplifier 42 across the fourth of the resistors 50.

It constitutes a summing network for the differential amplifier, which is of a conventional nature and whose four resistors can be approximately 1 kohm. The potentiometer makes it possible to adjust the continuous component of the signal supplied to the digitizer 18 by the amplifier 44.

The piezoelectric transducer 4 is provided with an electrical resistor 54, e.g. of 50 ohms, which is connected between the terminals of the transducer 4 and whose function is to polarize the non-inverting input of the preamplifier 42.

The transducer 4 is also associated with a circuit incorporating a capacitor 56 and an adjustable electrical resistor 58, said circuit behaving as a transducer and serving to make substantially identical the impedances connected to the inputs of the preamplifier 42.

One terminal of the switch 405 is connected to the inverting input of the preamplifier 42, as well as to a terminal of the switch 406, whose other terminal is grounded and connected to a terminal of the switch 407. The other terminal of the latter is connected to the non-inverting input of the preamplifier 42 and to a terminal of the switch 408.

One terminal of the transducer 4 is grounded, whilst its other terminal is connected to the other terminal of the switch 408, as well as to the common point of the emitters of the transistors 36a and 36b, across a resistor Rc, whose function is defined hereinafter.

It can be seen in FIG. 6 that the piezoelectric transducer 4 is also associated with an adjustable capacitor 60, together with a two-position switch 62. One terminal of the capacitor 56 and one terminal of the adjustable resistor 58 are grounded, whilst their other terminals are connected to the other terminal of the switch 405 and to one terminal of the switch 62. Another terminal of the latter is connected to a terminal of the adjustable capacitor 60, whose other terminal is grounded. Another terminal of the switch 62 is connected to the connection between the resistor Rc and the piezoelectric transducer 4.

When the capacitance of the capacitor 56 is below that of the transducer 4, the switch 62 is placed in position (1), so as to add the capacitance of the capacitor 60 to that of the capacitor 56. However, when the capacitance of the capacitor 56 is above that of the transducer 4, the switch 62 is placed in position (2), so as to add the capacitance of the capacitor 60 to that of the transducer 4.

The function of the isolating switch 40 is to isolate the adapting stages 38a and 38b from the residual noise of the generator 14, when the latter is inoperative, i.e. after it has supplied exciting signals to the transistors 38a and 38b. Thus, the signals supplied by the transducer 4, when it receives an ultrasonic echo, are weak and it is therefore appropriate to obtain freedom from the residual noise of the generator 14.

The function of the isolating switch 48 is to disconnect the transducer 4 from the preamplifier 42 when the transducer is in its transmission phase, because the preamplifier 42 only accepts low impedance input signals, whereas the transducer supplies high amplitude signals when said transducer is in its transmission phase.

A definition will be given hereinafter of the states of the eight switches 401 to 408 during the transmission, waiting and reception phases of the transducer, the waiting phase corresponding to the propagation time of the ultrasonic signals from the transducer to the reference reflector and from the latter to the transducer.

In the transmission phase, the switches 401, 404, 406 and 407 are switched on, whilst the switches 402, 403, 405 and 408 are switched off. In the waiting phase, the switches 402 and 403 are switched on, the switches 406 and 407 remain on, the switches 401 and 404 are switched off and the switches 405 and 408 remain off. In the reception phase, the switches 402 and 403 remain on, the switches 405 and 408 are switched on, the switches 401 and 404 remain off and the switches 406 and 407 are switched off.

The function of the resistor Rc will now be explained. The maximum value of the current which can be supplied by the source obtained with the bipolar transistors 38a and 38b is limited by the saturation current of said transistors.

In order to maintain the power stage formed by these two transistors in an approximately linear operating zone, it is appropriate to insert a low value electrical resistor, namely resistor Rc, between said power stage and the piezoelectric transducer 4.

The value of the resistor Rc is dependent on the value of the saturation current of the two bipolar transistors, the value of the shunt capacitance inherent in the transducer and the form of the exciting voltage $v(t)$ of said transducer and more particularly the maximum value of the gradient $dv/dt$ of said exciting voltage.

Figure 7:
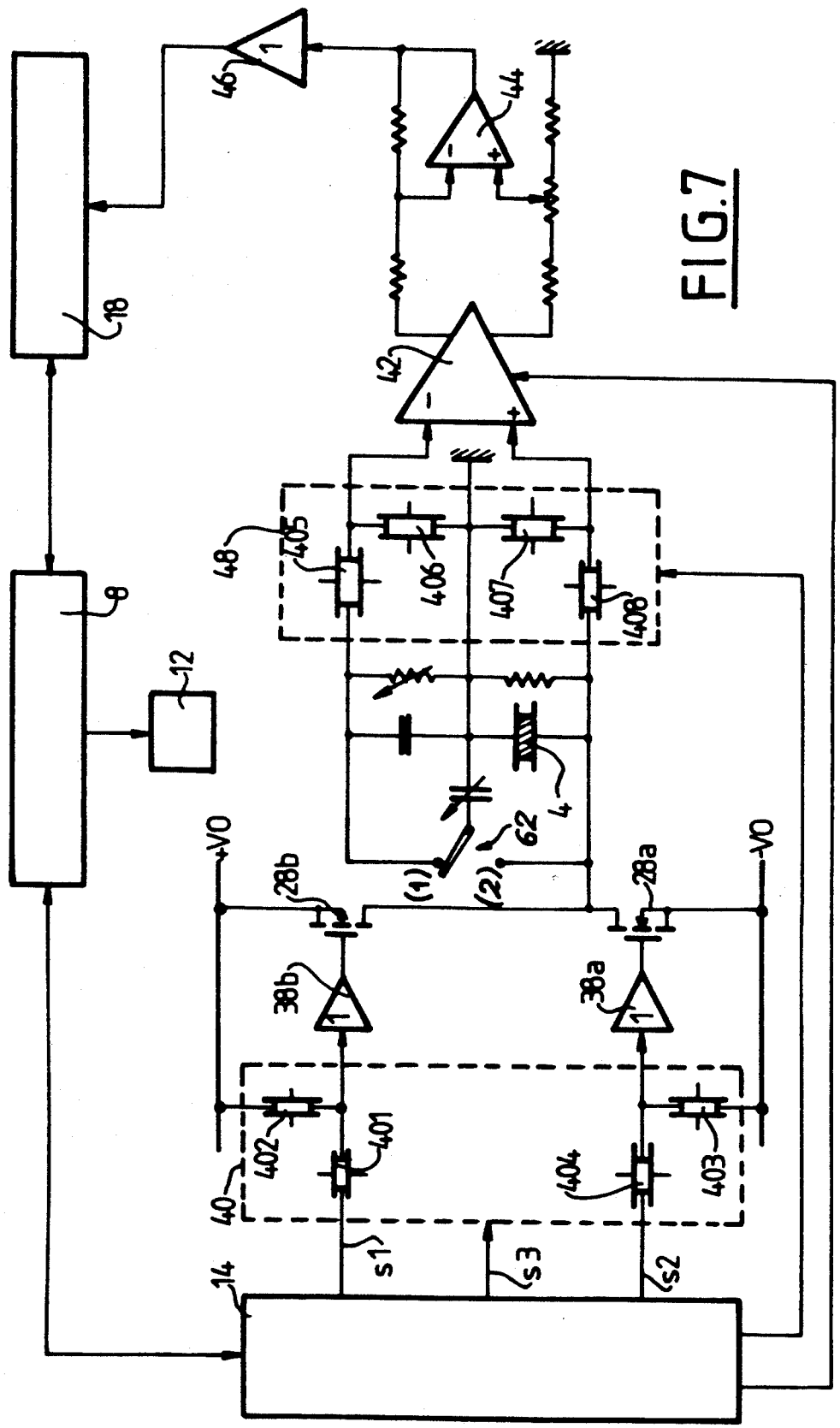
FIG. 7 A diagrammatic view of another embodiment using MOS transistors for asymmetrically exciting the piezoelectric transducer of the system shown in FIG. 7.

In the embodiment of the inventive system diagrammatically shown in FIG. 7, the piezoelectric transducer is still asymmetrically excited. In this system, the bidirectional current source is provided by two MOS power transistors and not two bipolar power transistors. They consist of transistors 28a and 28b, which have been described with reference to and are connected as in FIG. 3.

The output s1 of the generator 14 controls the gate of the transistor 28b across the adapting stage 38b and the output s2 of the generator 14 controls the gate of the transistor 28a across the adapting stage 38a.

In the system according to FIG. 7, there is no longer a resistor Rc. Whichever of the terminals of the transducer 4 is not grounded is connected to a terminal of the switch 62, as well as to the connection between the drains of the transistors 28a and 28b.

Moreover, in the system of FIG. 7, the four elementary switches 401 to 404 of the switch 40, which is interposed between the generator 14 and the adapting stages 38a and 38b, are connected in the manner described hereinbefore.

One terminal of the switch 401 is connected to the output s1 of the generator 14 and the other terminal of said switch 401 is connected to the input of the adapting stage 38b, as well as to a terminal of the switch 402, whose other terminal is raised to the same positive potential $+VO$ as the source of the transistor 28b.

One terminal of the switch 404 is connected to the output s2 of the generator 14 and the other terminal of said switch 404 is connected to the input of the adapting stage 38a, as well as to a terminal of the switch 403, whose other terminal is raised to the same negative potential $-VO$ as the source of the transistor 28a.

During the transmission, waiting and reception phases of the transducer 4, the "off" and "on" states of the four switches 401 to 404 and the four switches 405 to 408 are as indicated hereinbefore.

Figure 8:
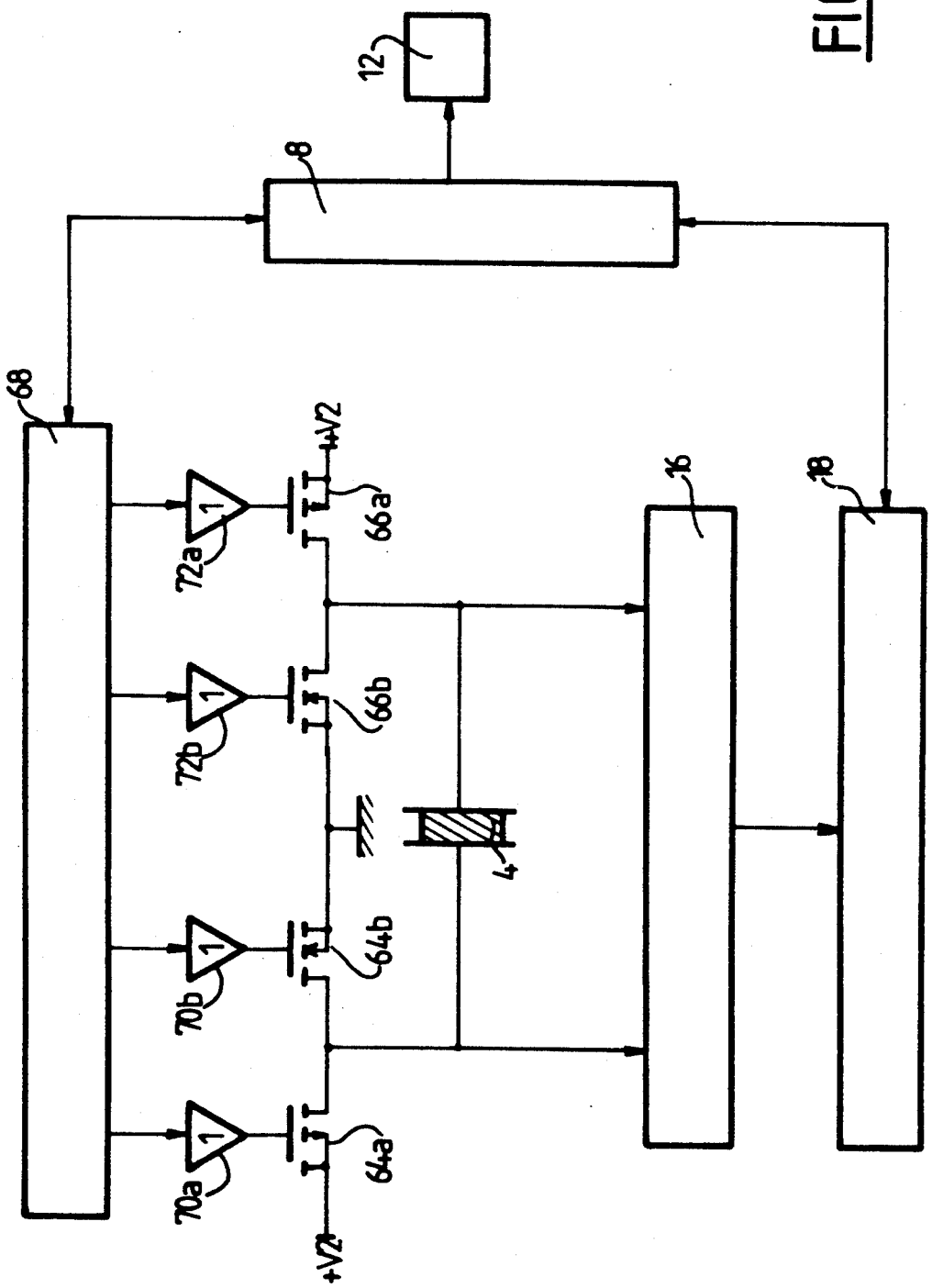
FIG. 8 Diagrammatically a system according to the invention using a symmetrical excitation of the system transducer.

FIG. 8 diagrammatically illustrates a system according to the invention in which the transducer 4 is symmetrically excited. In this case, use is made of two bidirectional current sources, each of them being connected with the aid of two unidirectional current sources, such as e.g. MOS power transistors, so that a first group of two MOS power transistors 64a, 64b and a second group of MOS power transistors 66a, 66b are obtained.

Use is made here of a generator with four outputs 68 and which is controlled by the computer 8 (said generator 68 being the homolog of the generator 14 of FIG. 3).

This generator 68 can e.g. be in the form of two double output, arbitrary function generators marketed by the LECROY company under reference 9100 and which are interconnected in master-slave manner.

For the acceleration of the convergence of the sequence referred to hereinbefore, it is then necessary to determine four correction functions respectively corresponding to the four transistors 64a, 64b, 66a and 66b and which are applied to the calculated signal X(t) prior to the supply of the latter to the generator 68 for exciting the current sources.

The four outputs of the generator 68 control the gates of the transistors 64a, 64b, 66a and 66b respectively across the power adapting stages 70a, 70b, 72a and 72b.

The signals supplied by the transducer 4 are again amplified by the amplifying means 16 and are then supplied to the computer 8 via the digitizer 18.

The transistors 64a and 66a are P channel MOS transistors, whilst the transistors 64b and 66b are N channel MOS transistors.

The source of each of the transistors 64a and 66a is raised to a positive potential +V2, whilst the source of each of the transistors 64b and 66b is grounded.

Finally, both the drains of the transistors 64a and 64b are connected to a terminal of the piezoelectric transducer 4 and the drains of the transistors 66a and 66b are both connected to the other terminal of the transducer 4.

The voltage appearing between the terminals of the transducer, when the latter receives an ultrasonic echo, is amplified by amplification means 16 and the thus amplified signal is supplied to the computer 8 across the digitizer 18.

Figure 9:
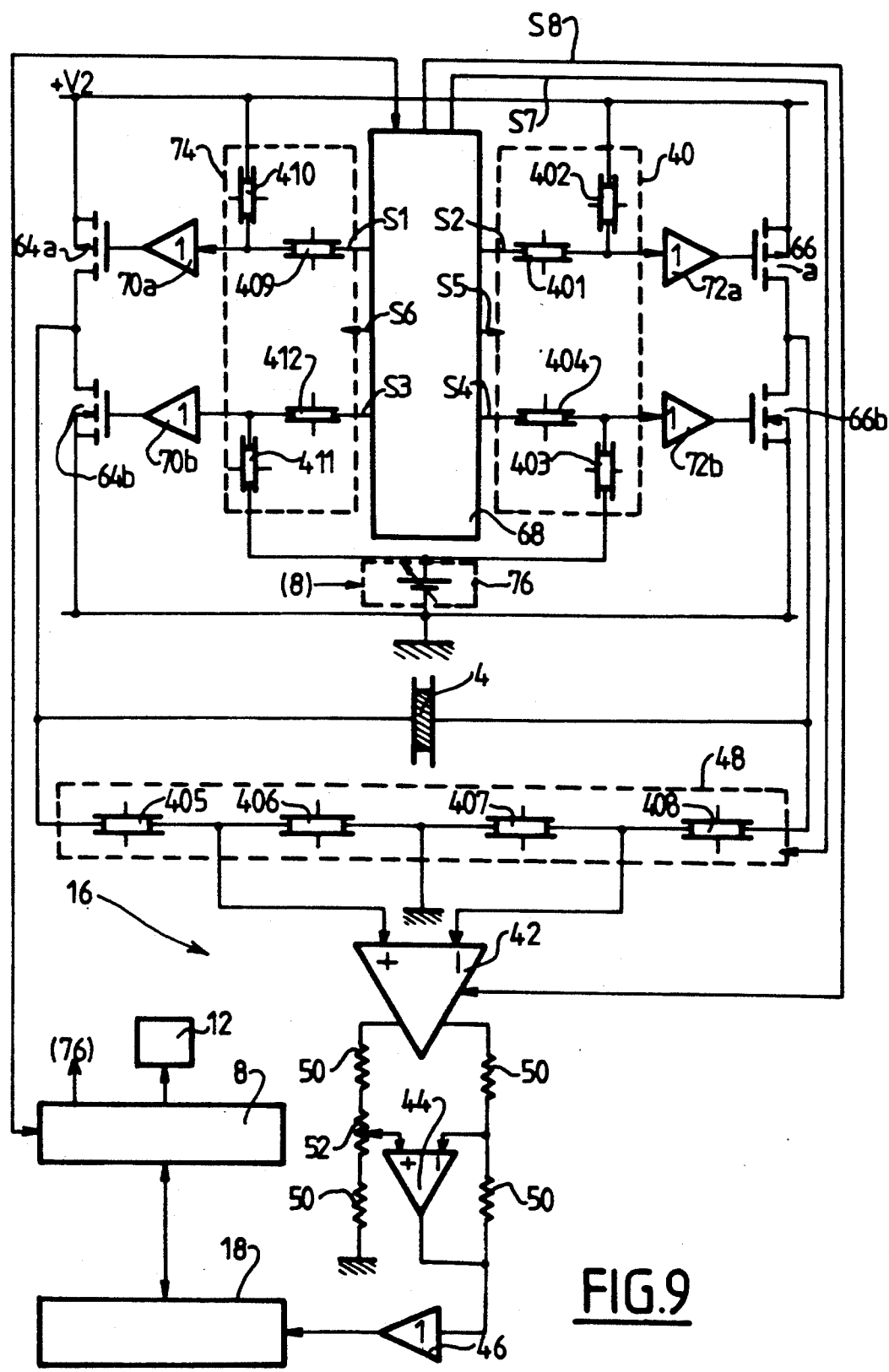
FIGS. 9 to 11 Diagrammatic views of embodiments of the system according to the invention, each using a symmetrical excitation of their piezoelectric transducer.

FIG. 9 diagrammatically shows an embodiment of the system according to the invention in which the piezoelectric transducer 4 is symmetrically excited.

The system diagrammatically shown in FIG. 9 has MOS power transistors 64a, 64b, 66a and 66b connected in the manner described hereinbefore and respectively controlled by the generator 68 across adapting stages 70a, 70b, 72a and 72b.

The amplification means 16 used in the system diagrammatically shown in FIG. 9 once again comprise the preamplifier 42 and the amplifier 44 equipped with resistors 50 and the potentiometer 52 arranged in the manner described relative to FIG. 6. The signal from the amplifier 44 is once again supplied to the digitizer 18 via the adapting stage 46.

In the system of FIG. 9, once again use is made of the analog isolating switch 40 comprising four elementary switches 401, 402, 403 and 404, as well as the analog isolating switch 48, which comprises the four elementary switches 405, 406, 407 and 408, as well as another analog isolating switch 74 also comprising four elementary switches 409, 410, 411 and 412.

The four outputs S1, S2, S3 and S4 of the generator 68 are respectively connected to the inputs of the adapting stages 70a, 72a, 70b and 72b.

The switch 74 is connected between the outputs S1 and S3 and the adapting stages 70a, 70b, whilst the switch 40 is connected between the outputs S2 and S4 and the adapting stages 72a, 72b. The switch 48 is connected between the piezoelectric transducer 4 and the preamplifier 42.

FIG. 9 shows that the generator 68 also has outputs S5, S6 and S7, which respectively supply logic control signals of the switches 40, 74 and 48, as well as an output S8 for controlling the gain of the preamplifier 42.

The adapting stages 70a, 70b, 72a and 72b can be of the type marketed by the HARRIS company under reference HA-5002 and the switch 74 can be of the type marketed by the HARRIS company under reference HI-201HS.

The terminal of the transducer 4, which is connected to the drains of the transistors 64a and 64b, is also connected to one terminal of the switch 405, whose other terminal is connected to the switch 406, as well as to the non-inverting input of the preamplifier 42. The other terminal of the transducer 4, which is connected to the drains of the transistors 66a and 66b, is also connected to one terminal of the switch 408, whose other terminal is connected to the inverting input of the preamplifier 42, as well as to a terminal of the switch 407. The two remaining terminals of the switches 406 and 407 are grounded.

One terminal of the switch 401 is connected to the output S2 of the generator 68, whilst its other terminal is connected to the adapting stage 72a, as well as to a terminal of the switch 402, whose other terminal is raised to the potential +V2.

One terminal of the switch 404 is connected to the output S4 of the generator 68, whilst its other terminal is connected to the input of the adapting stage 72b, as well as to one terminal of the switch 403.

One terminal of the switch 409 is connected to the output S1 of the generator 68, whilst its other terminal is connected to the input of the adapting stage 70a, as well as to one terminal of the switch 410, whose other terminal is raised to the potential +V2.

One terminal of the switch 412 is connected to the output S3 of the generator 68, whilst its other terminal is connected to the input of the adapting stage 70b, as well as to one terminal of the switch 411.

The system diagrammatically shown in FIG. 9 also incorporates a variable voltage source 76, which is electronically controlled by the computer and whose background noise is well below that of the generator 68, whose function is to convert in analog form the signal supplied by the computer 8 with a view to controlling the MOS power transistors 64a, 64b, 66a and 66b.

The negative terminal of the voltage source 76 is grounded, whilst the positive terminal of said source 76 raises the remaining terminals of the switches 403 and 411 to a positive potential vo.

The function of the analog switches 40 and 74, which are connected directly at the outputs of the generator 68, is to isolate, during the reception phase of the transducer, the input of the power stage (produced with MOS transistors) from the generator background noise.

As the power stage is permanently connected to the piezoelectric transducer 4, the use of the analog switches 40 and 74 makes it possible to eliminate the undesired, permanent dynamic connection due to the parasitic capacitances of the MOS power transistors 64a, 64b, 66a and 66b and makes it possible to improve the signal-to-noise ratio in such a way that it is possible to detect ultrasonic echos which lead, between the terminals of the piezoelectric transducer, to a voltage, whose peak-to-peak excursion can have an amplitude as low as 10 microvolts.

Details will now be given of the states of twelve elementary switches 401 to 412 during the transmission, waiting and reception phases of the piezoelectric transducer 4 of the system of FIG. 9.

During the transmission phase, the switches 401, 404, 409, 412, 406 and 407 are switched on, whilst the switches 402, 403, 410, 411, 405 and 408 are switched off.

During the waiting phase, the switches 402, 403, 410 and 411 are switched on, the switches 406 and 407 remain on, the switches 401, 404, 409 and 412 are switched off and the switches 405 and 408 remain off.

During the reception phase, the switches 402, 403, 410 and 411 remain on, the switches 405 and 408 are switched on, the switches 401, 404, 409 and 412 remain off and the switches 406 and 407 are switched off.

The function of the variable voltage source will now be described. This source makes it possible to control the transistors 64b and 66b during the reception phase of the piezoelectric transducer 4. Thus, during this reception phase, the switches 403 and 411 are switched on and consequently the voltage vo is imposed on the gate of the transistors 70b and 72b. Thus, the latter behave as drain-source resistors, whose value is controlled by the voltage vo, said drain-source resistors being connected, in the reception phase, between ground and the terminals of the transistor.

Figure 10:
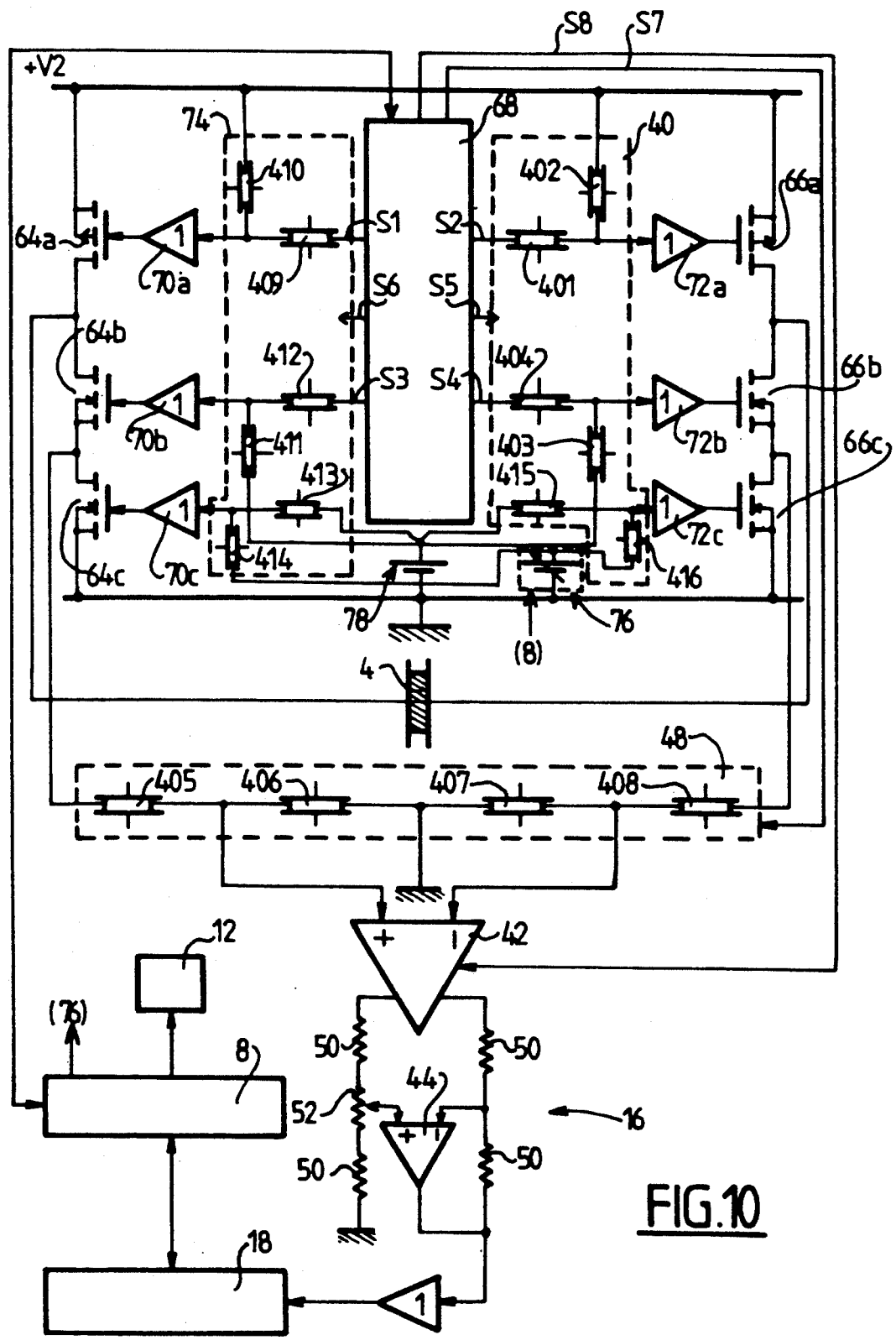

FIG. 10 diagrammatically shows another embodiment of the system according to the invention, in which the piezoelectric transducer 4 is once again symmetrically excited.

The system diagrammatically shown in FIG. 10 differs from that of FIG. 9 by the fact that it has two supplementary MOS power transistors 64c and 66c, as well as a fixed voltage source 78. In addition, in the generator of FIG. 10, the switch 74 has two supplementary elementary switches 413 and 414.

In the same way, the switch 40 has two supplementary switches 415 and 416. The transistors 64b, 64c, 66b and 66c are identical.

Details will now be given of the changes to the network affecting certain elements of the system of FIG. 10 compared with the system of FIG. 9.

In the case of the system of FIG. 10, the terminals of the piezoelectric transducer are no longer respectively connected to the switches 405 and 408 and the respective sources of the transistors 64b and 66b are no longer grounded.

The source of the transistor 64b is connected to the drain of the transistor 64c, as well as to one of the terminals of the switch 405 (whereof the other terminal is connected to the non-inverting input of the preamplifier 42). The source of the transistor 66b is connected to the drain of the transistor 66c, as well as to one of the terminals of the switch 408 (whereof the other terminal is connected to the inverting input of the preamplifier 42).

It can also be seen that the connections of the switches 403 and 411, as well as those of the variable voltage source 76 are different.

One terminal of the switch 403 (whose other terminal is connected to the switch 404) is connected to the positive terminal of the voltage source 78. One terminal of the switch 411 (whose other terminal is connected to the switch 412) is also connected to the positive terminal of the voltage source 78. The negative terminal of said voltage source 78, as well as the source of each of the transistors 64c and 66c are grounded.

Moreover, the system of FIG. 10 also has two more adapting stages than the system of FIG. 9, said supplementary adapting stages being designated 70c and 72c.

One terminal of the switch 413 is connected to the positive terminal of the voltage source 78 and the other terminal of said switch 413 is connected to a terminal of the switch 414, as well as to the input of the adapting stage 70c, whose output is connected to the gate of the transistor 64c.

One terminal of the switch 415 is connected to the positive terminal of the voltage source 78 and the other terminal of said switch 415 is connected to one terminal of the switch 416, as well as to the input of the adapting stage 72c, whose output is connected to the gate of the transistor 66c.

The remaining terminals of the switches 414 and 416 are connected to the positive terminal of the variable voltage source 76, whose negative terminal is grounded. The adapting stages 70c and 72c are identical to the adapting stages 70b and 72b.

Details will now be given of the states in which must be located the elementary switches of the system of FIG. 10 during the transmission, waiting and reception phases of the piezoelectric transducer 4.

During the transmission phase, the switches 401, 404, 415, 409, 412, 413, 406 and 407 are switched on and the switches 402, 403, 416, 410, 411, 414, 405 and 408 are switched off. During the waiting phase, the switches 402, 403, 410 and 411 are switched on, the switches 415, 413, 406 and 407 remain on, switches 401, 404, 409 and 412 are switched off and the switches 416, 414, 405 and 408 remain off. During the reception phase, the switches 416, 414, 405 and 408 are switched on, the switches 402, 403, 410 and 411 remain on, the switches 415, 413, 406 and 407 are switched off and the switches 401, 405, 409 and 412 remain off.

During the transmission phase of the transducer 4, the voltage source 78 supplies to the input of the adapting stages 70c and 72c a positive voltage v1, which can be approximately 15 V and the transistors 64c and 66c are conductive and virtually behave as short-circuits. The drain-source resistor, generally called Rdson resistance, of these transistors 64c and 66c in the on state is very low and is e.g. approximately 10 milliohms.

During said transmission phase of the transducer 4, the transistors 64a, 64b, 66a and 66b are controlled by signals from the generator 68.

During the waiting phase of the transducer 4, the transistors 64c and 66c virtually behave as short-circuits, the transistors 64b and 66b become short-circuits, their Rdson resistance then e.g. being approximately 10 milliohms) and the transistors 64a and 66a become open circuits.

During the reception phase of the transducer 4, the transistors 64c and 66c have a higher Rdson resistance, which can be approximately 25 ohms, the gates of the transistors 64c and 66c being connected across adapting stages 70c and 72c and switches 414 and 416 to the positive terminal of the voltage source 76, which is regulated by the computer 8. During this reception phase, the transistors 64b and 66b are virtually short-circuits and the transistors 64a and 66a are open circuits.

Thus, during the transmission phase, the voltage applied between the transducer terminals for exciting said transducer can be subject to considerable variations without affecting the preamplifier 42.

During the transducer reception phase, the background noise of the generator 68, which is present at the outputs S1, S2, S3 and S4 of the latter is prevented from reaching the piezoelectric transducer 4 by the switches 40 and 74.

In the case of a symmetrical excitation of the piezoelectric transducer 4, the peak-to-peak excursion of the exciting voltage between the terminals of said transducer 4 is twice its supply voltage, which represents the advantage of systems such as those shown in FIGS. 9 and 10 compared with those of the type shown in FIGS. 6 and 7. It should also be noted that the system of FIG. 10 has advantages compared with the system of FIG. 9.

Thus, the use of supplementary transistors 64c and 66c, which virtually behave as short-circuits during the transmission phase, give a supplementary isolation level between the piezoelectric transducer 4 and the inputs of the preamplifier 42.

However, it should be noted that in a large number of applications, the switch 48 used in the systems of FIGS. 9 and 10 is not necessary, which makes it possible to simplify the construction of such systems.

Another advantage of the system of FIG. 10 compared with that of FIG. 9 is that the analog voltage present between the terminals of the transducer 4 during the excitation of the latter can exceed the maximum analog voltage accepted by the analog switch 48, due to the use of the supplementary transistors 64c and 66c.

The value of the gain of the preamplifier 42 and the characteristics of the observation time window (time interval during which the ultrasonic echo is detected), said characteristics namely being the width of said window and the delay of the start of reception compared with the end of transmission, are controlled by the computer 8.

The dead time necessary for the switching of the gain of the preamplifier 42 is below 400 ns, so that it is conceivable to switch this gain by means of the same observation time window in applications where this proves necessary.

Figure 5:
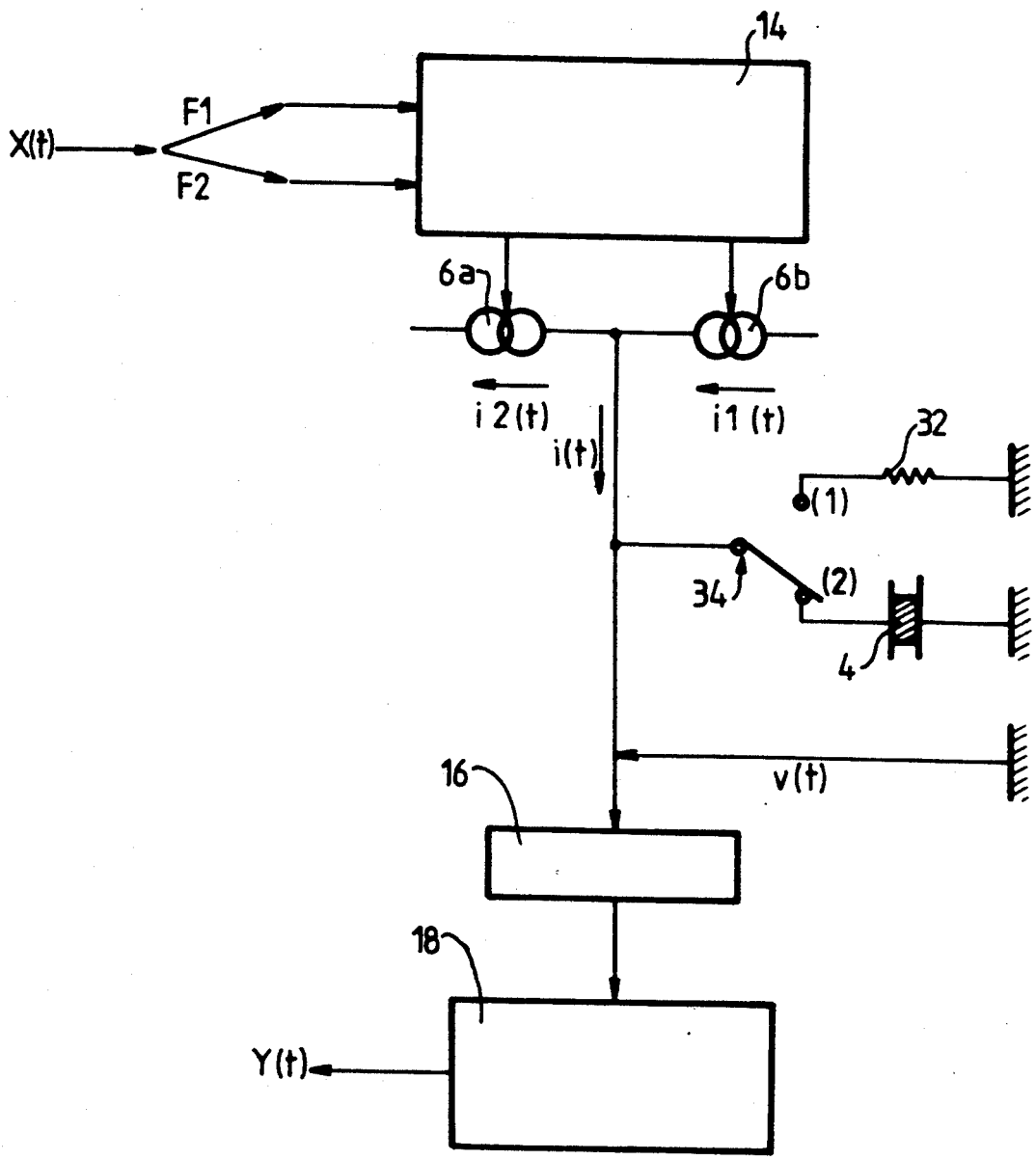
FIG. 5 Diagrammatically a system according to the invention permitting an acceleration of said algorithm.

In the systems shown in FIGS. 6, 7, 9 and 10, it would obviously be possible to speed up the convergence of the sequence referred to hereinbefore and use would then be made of the switch 34 of FIG. 5 (associated with the resistor 32), which would be connected in such a way that the resistor 32 of FIG. 5 can be substituted for the piezoelectric transducer 4 under the control of the computer 8.

The aforementioned systems according to the invention give an absolute control of the time or spectral content of the transmitted ultrasonic signal. These systems make it possible to adapt the piezoelectric transducer exciting signal no matter which transducer is used for the purposes of a given ultrasonic test and in accordance with the criterion specified by the user.

This criterion can be the time form of the ultrasonic echo returned by the reference reflector or the spectral band or bands in which the user wishes to carry out the test.

These systems according to the invention consequently make it possible to carry out broad band, single narrow band or multiple narrow band ultrasonic inspections and tests.

With a system according to the invention, the problem of the physical damping inherent in the piezoelectric transducer is no longer critical, no matter what the resonant frequency of the piezoelectric pellet used for producing said transducer and the standard problem of electrical adaptation associated with each transducer no longer exists. This makes it possible to reduce difficulties and therefore the manufacturing costs for the transducers.

The transmitting part of the system can be entirely integrated into all applications where it is sufficient to have an exciting signal, whose maximum voltage peak-to-peak excursion value at the terminals of the transducer does not exceed ±20 V. For such an integration, it is possible to use the library of precharacterized cells produced in BICMOS technology by SGS-THOMSON.

Figure 11:
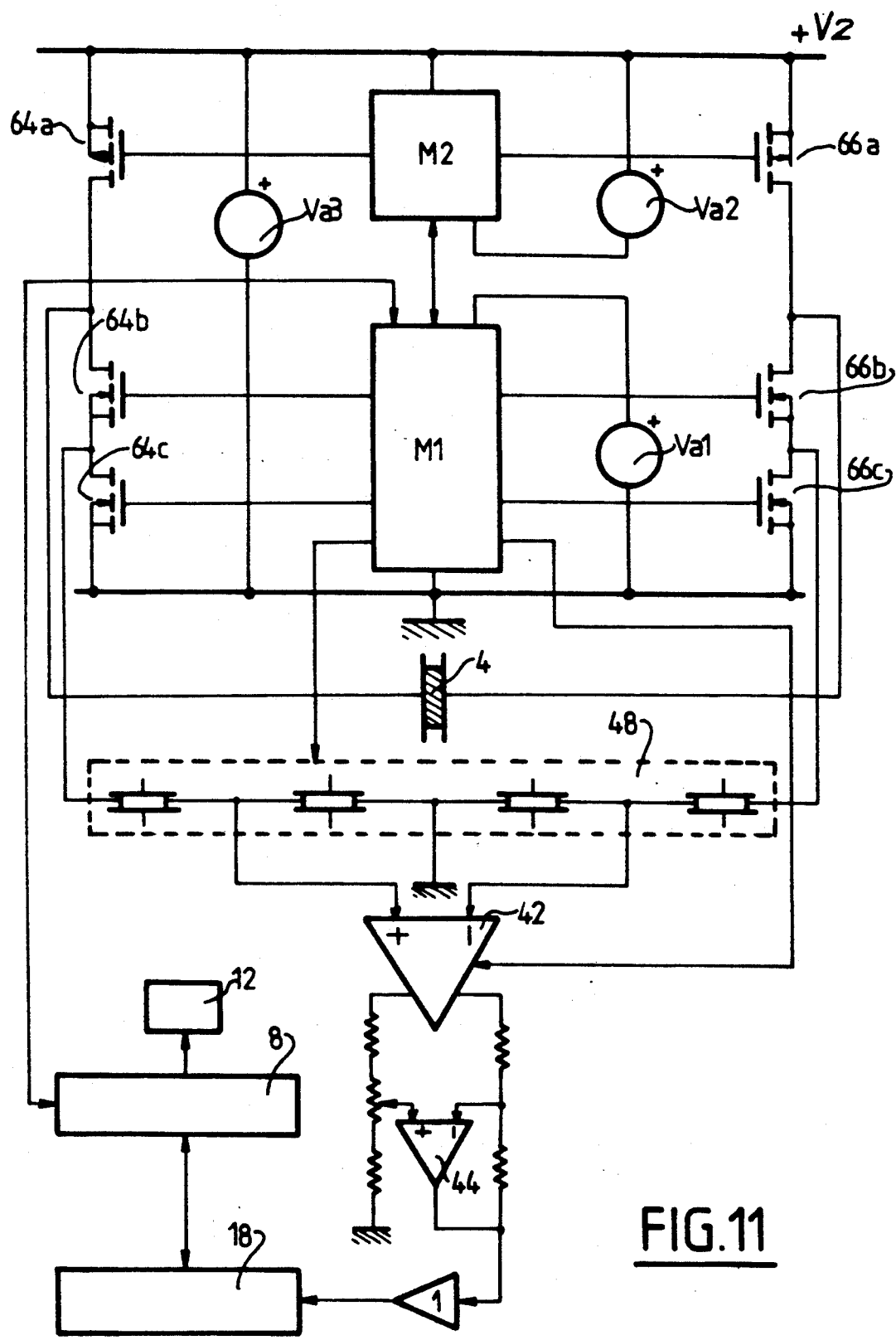

For applications requiring a higher excitation level, e.g. ±20 to ±500 V, the transmitting part, i.e. in the case of FIG. 10, the generator 68, the switches 40 and 74 and the adapting stages 70a, 70b, 70c, 72a, 72b and 72c can be integrated in the form of two modules M1 and M2, as can be seen in FIG. 11. The sources 76 and 78 of FIG. 10 are not shown in FIG. 11.

The module M1, whose reference is ground, controls the gate of the N channel MOS power transistors and the module M2, which is at floating potential, controls the gate of the P channel MOS power transistors.

The supply voltages of these two modules M1 and M2, which are designated Va1 and Va2, can under these conditions be limted to approximately 20 V, which allows the integration using conventional technology.

The sources of the transistors 64a and 66a are raised to the high potential V2 by means of a supply Va3.

Existing technology for the manufacture of MOS power transistors makes it possible to reach a potential V2 of approximately 500 V, whilst maintaining a maximum gate control voltage of approximately 10 V and a pulse-type current of a few dozen amperes, associated with a Rdson resistance of approximately 10 milliohms.

For applications where a high exciting voltage and integration into a single circuit is indispensable, the high voltage technology called HVIC and developed by the International Rectifier Company can be used. In this case, it is also desirable to integrate, on a same integrated circuit, the means for amplifying the signals supplied by the transducer during the reception of the ultrasonic echo, as well as the corresponding analog isolating switch.

The complete transmission-reception electronics can then be placed against the piezoelectric pellet of the transducer, which makes it possible to optimize its operating conditions.

In this connection, it is pointed out that the computer, the LECROY arbitrary function generator and the aforementioned TEKTRONIX device could obviously be replaced by simpler means permitting the realization of the systems of FIGS. 6 and 7 and made much more compact than the aforementioned devices.

The present invention is not limited to a system using a single transducer for the transmission and reception of ultrasonics during an ultrasonic test.

Figure 12:
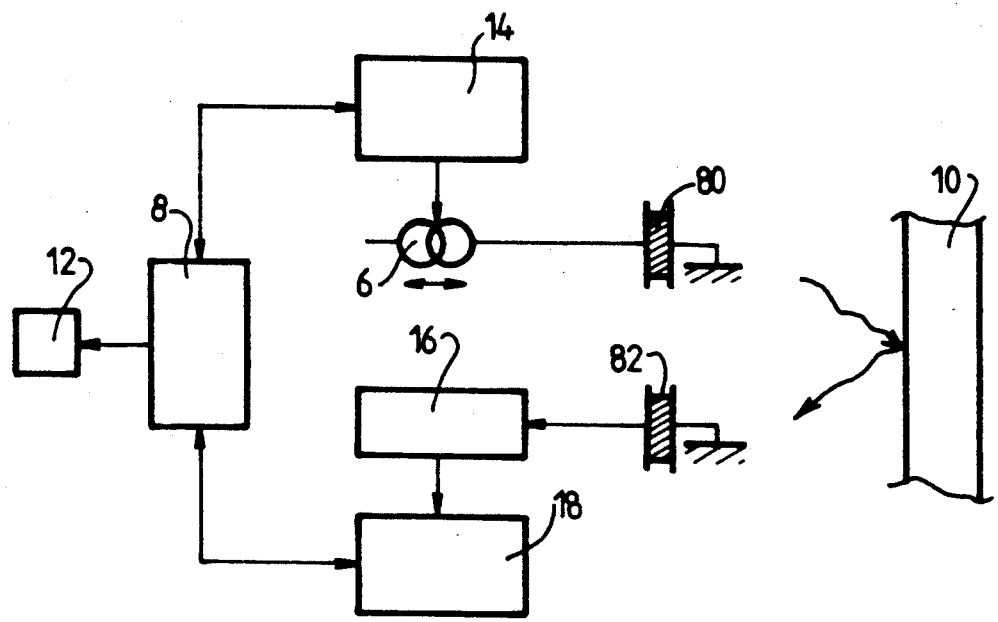
FIG. 12 Diagrammatically a system according to the invention using a transmitting piezoelectric transducer and a receiving piezoelectric transducer operating in reflection.

FIG. 12 shows a system according to the invention, which comprises a piezoelectric transducer 80 controlled by the bidirectional current source 6 and which transmits ultrasonics to the reference reflector 10 and another piezoelectric transducer 82, which receives the ultrasonic echo supplied by said reference reflector 10, the signal detected by said transducer 82 then being supplied to the amplification means 16.

Figure 13:
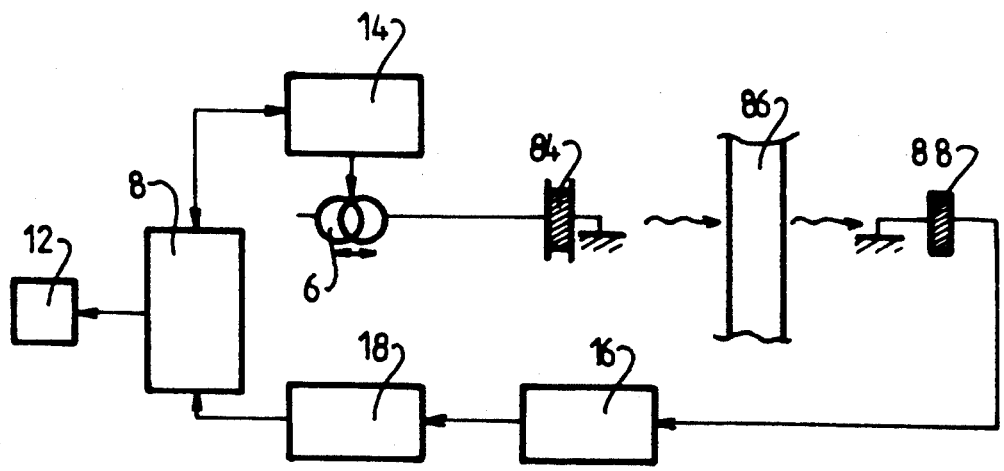
FIG. 13 Diagrammatically another system according to the invention using a transmitting piezoelectric transducer and a receiving piezoelectric transducer operating in transmission.

Another system according to the invention and diagrammatically shown in FIG. 13 makes it possible to operate by transmission and to this end comprises a piezoelectric transducer 84, which is excited by the bidirectional current source 6 and which supplies ultrasonics to a reference object 86 and another piezoelectric transducer 88, which receives ultrasonics transmitted by the reference object 86, the transducers 84 and 88 then being placed on either side of the reference object 86. The signal detected by the transducer 88 is obviously supplied to the amplification means 16.

I claim:

1. Ultrasonic transmission-reception system comprising ultrasonic transmission-reception means having a piezoelectric transducer for at least transmitting ultrasonic waves and an electric current generator for exciting said transducer so that said transducer transmits an ultrasonic wave, wherein said system also has electronic processing means able to determine in an approximate manner and stored at least one current generator exciting signal, said exciting signal being associated with reference object and leading to a predetermined shape of a detected ultransonic wave from said object following the interaction of said object with said ultrasonic wave produced by said transducer as a result of the excitation of said current generator.

2. System according to claim 1, wherein an electronic processing means is provided for determining the inverse function $H^{-1}$ of the transfer function H of the process which, with a signal X for exciting said current generator (6, 6a-6b, 28a-∞b, 36a-36b, 64a-64b 66a-66b), associates the signal Y=H(X) detected by the reception means, said function $H^{-1}$ being determined on the basis of a signal Xo for the initial excitation of said current generator and on the basis of a detected signal H(Xo), assuming the function H to be linear and independent of time and then, by an iteration method, an approximation Xn of said exciting signal associated with said reference object, on the basis of a signal X1 taken as equal to the image, by the function $H^{-1}$, of a predetermined ultrasonic wave shape and by correcting, during each iteration stage, the approximation of said signal for exciting said current generator obtained in the preceding stage by the image, by the function $H^{-1}$, of the error committed in said preceding stage on said predetermined ultransonic wave shape.

3. System according to claim 1, wherein said current generator having at least one bidirectional current source for exciting said transducer.

4. System according to claim 3, wherein each bidirectional source is constituted by two undirectional current sources (6a-6b, 28a-28b, 36a-36b, 64a-64b, 66a-66b).

5. System according to claim 4, wherein each undirectional source has a MOS transistor (28a, 28b, 64a, 66a, 66b).

6. System according to claim 1, wherein said transducer (4) is a transducer for the transmission and repection of ultrasonic waves.

7. System according to claim 1, wherein said current generator (6, 6a-6b, 28a-28b, 36a -36b) excites said transducer (4) in an asymmetrical manner.

8. System according to claim 1, wherein said current generator has two bidirectional current sources (64a-64b, 66a-66b) for exciting the transducer (4) in symmetrical manner.

9. System according to claim 6, wherein said transmission-reception means also comprise means for amplifying said ultrasonic waves detected by said transmission-reception means, and switching means able to isolate an amplification means from said transducer, when said transducer transmits an ultrasonic wave.

10. System according to claim 6, wherein said transmission-reception means also comprises means for controlling said current generator, said control means receiving at the input, signals from said electronic processing means and used for exciting said current generator and supplying at the output, current generator exciting signals, and other switching means able to isolate said control means from said transducer, when said transducer receives an ultrasonic wave.

11. System according to claim 2, wherein said electronic processing means also determine a transformation of said current generator exciting signal, whose composition with the transfer function H is approximately linear.

12. System according to claim 11, further comprising an electrical resistor and a two-position switch, namely a first position in which said switch connects said current generator to said electrical resistor to feed into said resistor the current supplied by said current generator and a second position in which said switch connects said current generator to said transducer for exciting said transducer, said electronic processing means being able to determine, when said switch is in said first position, and store a transformation of said signal for exciting said current generator, which enables the current supplied by said current said generator to vary linearly as function of said current generator exciting signal.

* * * * *